(12) United States Patent
Lewkowicz et al.

(10) Patent No.: US 7,727,169 B1
(45) Date of Patent: Jun. 1, 2010

(54) DEVICE FOR IN VIVO SENSING

(75) Inventors: Shlomo Lewkowicz, Tivon (IL);
Arkady Glukhovsky, Nesher (IL);
Harold Jacob, Jerusalem (IL)

(73) Assignee: Given Imaging, Ltd., Yoqneam (IL)

( * ) Notice: Subject to any disclaimer, the term of this patent is extended or adjusted under 35 U.S.C. 154(b) by 781 days.

(21) Appl. No.: 10/166,025

(22) Filed: Jun. 11, 2002

Related U.S. Application Data

(60) Provisional application No. 60/296,769, filed on Jun. 11, 2001.

(51) Int. Cl.
*A61B 5/103* (2006.01)
*A61B 5/117* (2006.01)

(52) U.S. Cl. ............... 600/593; 600/109; 600/160

(58) Field of Classification Search ......... 600/407, 600/301–302, 476, 104, 109, 114–117, 143, 600/151, 160, 561, 593, 101, 106, 590; 128/899, 128/903
See application file for complete search history.

(56) References Cited

U.S. PATENT DOCUMENTS

| | | | |
|---|---|---|---|
| 2,508,690 A * | 5/1950 | Schmerl | 604/265 |
| 3,683,389 A | 8/1972 | Hollis | |
| 3,971,362 A | 7/1976 | Pope et al. | |
| 4,028,687 A * | 6/1977 | Hamaguchi et al. | 340/870.16 |
| 4,278,077 A | 7/1981 | Mizumoto | |
| 4,389,208 A * | 6/1983 | LeVeen et al. | 604/95.03 |
| 4,439,197 A * | 3/1984 | Honda et al. | 604/891.1 |
| 4,689,621 A | 8/1987 | Kleinberg | |
| 4,741,327 A | 5/1988 | Yabe | |
| 4,844,076 A | 7/1989 | Lesho et al. | |
| 4,936,823 A * | 6/1990 | Colvin et al. | 600/7 |
| 5,279,607 A | 1/1994 | Schentag et al. | |
| 5,316,015 A * | 5/1994 | Sinaiko | 600/582 |
| 5,395,366 A * | 3/1995 | D'Andrea et al. | 604/890.1 |
| 5,395,390 A * | 3/1995 | Simon et al. | 623/1.18 |
| 5,398,670 A * | 3/1995 | Ortiz et al. | 600/114 |
| 5,595,565 A * | 1/1997 | Treat et al. | 600/114 |
| 5,604,531 A | 2/1997 | Iddan et al. | |
| 5,662,587 A | 9/1997 | Grundfest et al. | |
| 5,697,384 A * | 12/1997 | Miyawaki et al. | 128/899 |
| 5,819,736 A | 10/1998 | Avny et al. | |
| 5,833,603 A * | 11/1998 | Kovacs et al. | 600/317 |
| 5,906,591 A * | 5/1999 | Dario et al. | 604/95.03 |

(Continued)

FOREIGN PATENT DOCUMENTS

DE 344 0177 11/1984

(Continued)

OTHER PUBLICATIONS

Office Action for U.S. Appl. No. 10/694,092, mailed on Dec. 10, 2004.

(Continued)

*Primary Examiner*—Max Hindenburg
*Assistant Examiner*—Rene Towa
(74) *Attorney, Agent, or Firm*—Pearl Cohen Zedek Latzer, LLP

(57) ABSTRACT

A moveable in vivo device comprises a device body and at least one moveable appendage that is moveably coupled the device body such that movement of the moveable appendage causes the device body to move in a body lumen.

15 Claims, 3 Drawing Sheets

U.S. PATENT DOCUMENTS

| | | | |
|---|---|---|---|
| 5,993,378 A | | 11/1999 | Lemelson |
| 6,007,482 A * | | 12/1999 | Madni et al. ............... 600/115 |
| 6,138,604 A * | | 10/2000 | Anderson et al. ........... 114/332 |
| 6,162,171 A | | 12/2000 | Ng et al. |
| 6,240,312 B1 * | | 5/2001 | Alfano et al. ............... 600/476 |
| 6,285,897 B1 * | | 9/2001 | Kilcoyne et al. ............ 600/350 |
| 6,402,686 B1 | | 6/2002 | Ouchi |
| 6,402,687 B1 * | | 6/2002 | Ouchi ......................... 600/139 |
| 6,428,469 B1 * | | 8/2002 | Iddan et al. ................. 600/109 |
| 6,547,723 B1 * | | 4/2003 | Ouchi ......................... 600/146 |
| 6,632,175 B1 | | 10/2003 | Marshall |
| 6,719,684 B2 | | 4/2004 | Kim et al. |
| 6,783,499 B2 * | | 8/2004 | Schwartz .................... 600/486 |
| 6,950,690 B1 * | | 9/2005 | Meron et al. ................ 600/424 |
| 2001/0017649 A1 | | 8/2001 | Yaron |
| 2001/0051766 A1 | | 12/2001 | Gazdzinski |
| 2002/0103417 A1 | | 8/2002 | Gazdzinksi |
| 2002/0214580 | | 11/2002 | Iddan |
| 2002/0198439 A1 | | 12/2002 | Mizuno |
| 2003/0013370 A1 | | 1/2003 | Glukhovsky |
| 2003/0018280 A1 | | 1/2003 | Lewkowicz et al. |
| 2003/0045790 A1 | | 3/2003 | Lewkowicz et al. |
| 2003/0069474 A1 | | 4/2003 | Couvillon, Jr. |
| 2003/0167000 A1 * | | 9/2003 | Mullick et al. .............. 600/424 |
| 2003/0171648 A1 | | 9/2003 | Yokoi et al. |
| 2003/0171649 A1 | | 9/2003 | Yokoi et al. |
| 2003/0171652 A1 | | 9/2003 | Yokoi et al. |
| 2003/0195415 A1 | | 10/2003 | Iddan |
| 2003/0208107 A1 * | | 11/2003 | Refael ......................... 600/300 |
| 2003/0214579 A1 | | 11/2003 | Iddan |
| 2003/0216622 A1 * | | 11/2003 | Meron et al. ................ 600/300 |
| 2004/0027459 A1 | | 2/2004 | Segawa et al. |
| 2004/0162501 A1 * | | 8/2004 | Imran .......................... 600/547 |
| 2004/0176664 A1 | | 9/2004 | Iddan |

FOREIGN PATENT DOCUMENTS

| | | |
|---|---|---|
| DE | 34 40 177 | 5/1986 |
| IL | 143259 | 5/2001 |
| JP | 57-45833 | 3/1982 |
| JP | HEI 3-289779 | 12/1991 |
| JP | 4109927 | 4/1992 |
| JP | HEI 4-109927 | 4/1992 |
| JP | 1992-144533 | 5/1992 |
| JP | HEI 4-180736 | 6/1992 |
| JP | 5015515 | 1/1993 |
| JP | 06-114036 | 4/1994 |
| JP | 7289504 | 11/1995 |
| JP | 2001137182 | 5/2001 |
| JP | 2001 224551 | 8/2001 |
| JP | 2001224553 | 8/2001 |
| WO | WO 92/21307 | 12/1992 |
| WO | WO 98/11816 | 3/1998 |
| WO | WO 9930610 A1 * | 6/1999 |
| WO | WO 01/08548 | 2/2001 |
| WO | WO 01/50941 | 7/2001 |
| WO | WO 01/65995 | 9/2001 |
| WO | WO 01/87377 | 11/2001 |
| WO | WO 02/26103 | 4/2002 |
| WO | WO 02/067593 | 8/2002 |
| WO | WO 2004/028336 | 4/2004 |

OTHER PUBLICATIONS

"Electroactive Polymer Actuators as Artificial Muscles", Y. Bar-Cohen, Ed. Spie Press, 2001.

"The 'Elephant Trunk' Manipulator, Design and Implementation", M.W. Hannan and I D. Walker.

Robots for the future—Shin-ichi, et al., Nov. 29, 2001.

Video Camera to "TAKE"—RF System lab, Dec. 25, 2001.

www.rfnorkia.com—NORIKA3, Dec. 24, 2001.

U.S. Appl. No. 10/213,345, Glukhovsky.

Wellesley company sends body montiors into space, Crum, Apr. 1998.

Wireless transmission of a color television moving image from the stomach using a miniature CCD camera, light source and microwave transmitter. Swain CP, Gong F, Mills TN. Gastrointest Endosc 1997;45:AB40.

BBC News Online—Pill camera to 'broadcast from the gut', Feb. 21, 2000, www.news.bbc.co.uk.

* cited by examiner

DEVICE FOR IN VIVO SENSING

PRIOR PROVISIONAL APPLICATION

The present invention claims benefit of prior U.S. provisional application No. 60/296,769, entitled "A METHOD FOR MOVING AN OBJECT IN A BODY LUMEN", filed on 11 Jun. 2001.

FIELD OF THE INVENTION

The present invention relates to the field of in vivo sensing, to a method for moving an object in vivo and more specifically, to moving, for example, an imaging device in-vivo.

BACKGROUND OF THE INVENTION

In vivo sensors are non invasive tools used in diagnosis of diverse body systems. For example, swallowable devices may be used for sensing in vivo conditions in the gastrointestinal tract, such as, temperature, pH or pressure. Imaging devices such as imaging capsules can be used for imaging the gastrointestinal tract.

A capsule comprising a sensor may be swallowed and moved passively through the small intestine by peristalsis while sensing the entire small intestine. However, passive movement of objects through larger body lumens may be slow and unpredictable.

Current methods of moving objects, especially imaging devices, through body lumens usually include the use of devices such as stents, catheters, push-endoscopes, etc. These devices may be inconvenient for patient use, and may not always enable to reach distal parts of the body lumen.

SUMMARY OF THE INVENTION

A diagnostic or therapeutic device that is moveable through a body lumen may be able to access remote or difficult to access parts of the body lumen more efficiently than a passive object, thereby enabling effective operation of the device in diagnosing and/or providing treatment in the body lumen.

There is therefore provided, according to an embodiment of the invention, an object that is moveable in a body lumen. According to another embodiment there is provided a method for moving an object in a body lumen. In one embodiment, the object is a diagnostic or therapeutic or a combined diagnostic and therapeutic device. Thus, in accordance with an embodiment of the invention, an in vivo sensing device, such as an imaging device, that is moveable in a body lumen is provided. Further provided, according to an embodiment of the invention, is a method for sensing a body lumen by moving an in vivo sensing device, such as an imaging device, in the body lumen.

BRIEF DESCRIPTION OF THE DRAWINGS

The present invention will be understood and appreciated more fully from the following detailed description taken in conjunction with the drawings in which.

DETAILED DESCRIPTION OF THE INVENTION

A moveable object, according to an embodiment of the invention, comprises an object body and at least one moveable appendage. According to one embodiment the object body and moveable appendage are moveably coupled such that movement of the moveable appendage causes the object body to move in the body lumen environment. Typically, the object is an autonomous object that can be moved in or through a body lumen independently of external support. Preferably, movement of the moveable appendage causes the moveable appendage to press against the body lumen wall, thereby dislodging the object from the body lumen wall.

The moveable appendage, which is preferably made of pliant material, such as rubber or silicone, may be of any shape that is useful for moving the object, for example, a cone shaped appendage. Further, the moveable appendage may be an integral part of the object body or attached to the object body. The moveable appendage may be attached to the object body at any location or locations on the object body that are efficient in conveying movement to the object body, such as at an end of the object body along the longitudinal axis of the object.

According to one embodiment of the invention the method for moving an object having at least one moveable appendage, in a body lumen, comprises the steps of causing the at least one moveable appendage to move. The moveable appendage can be caused to move by an actuator that is in communication with a lever system that moveably couples the moveable appendage and the object body. Alternatively, the moveable appendage may be made of configurally changeable material, such as bimorph material, and the step of causing the appendage to move comprises creating a condition suitable for a configuration change by the configurally changeable material.

In one embodiment of the invention the object is a sensing device, such as an imaging device. However, other objects and sensing devices, such as temperature sensing devices, pH sensing device, pressure sensing devices and others, may be included in the invention. According to an embodiment of the invention, an in vivo sensor is housed in a device body, which may be of any suitable size or design for being moved in or through a body lumen (for example, the housing may be a capsule, pill, needle, stent, catheter, etc.). The device, which is typically an autonomous device, further includes means for moving the device in or through the body lumen.

According to further embodiments, the invention provides a method for is imaging a body lumen by moving an imaging device, having at least one moveable appendage, in the body lumen. The method comprises the steps of causing the moveable appendage to move and obtaining images of the body lumen.

Figure 1:
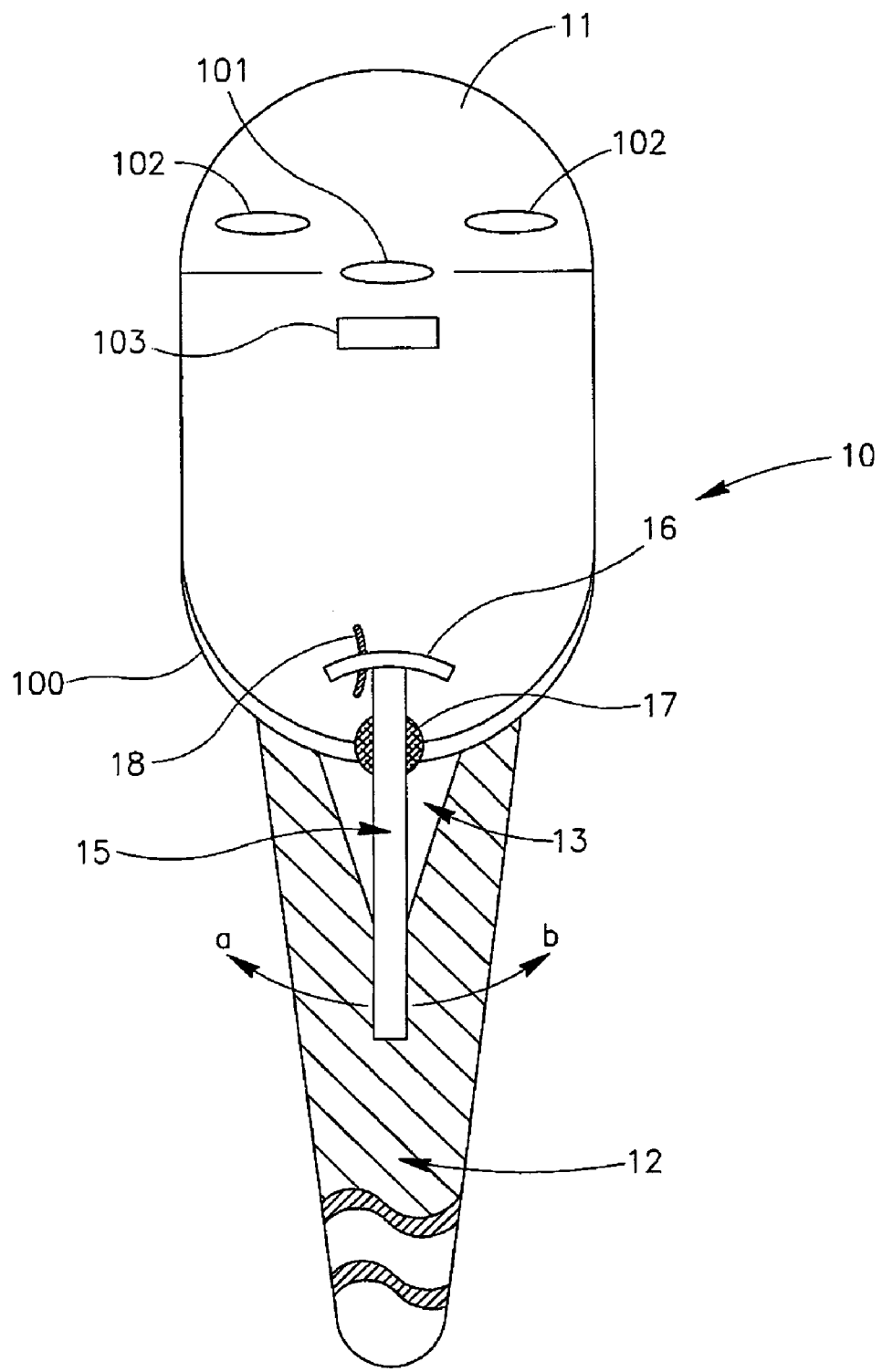
FIG. 1 is a schematic illustration of an object that is movable in a body lumen, in accordance with an embodiment of the invention.

A capsule shaped imaging device, according to an embodiment of the invention, is schematically illustrated in FIG. 1. Imaging devices suitable for use in this invention, for example, are described in co pending U.S. patent application Ser. No. 09/800,470 (WO 01/65995), and in U.S. Pat. No. 5,604,531 to Iddan, both of which are hereby incorporated by reference. The imaging device allows the obtaining of in vivo images from within body lumens or cavities, such as images of the gastrointestinal (GI) tract. According to one embodiment the imaging device contains an imaging system, at least one illumination source and a transmitter for transmitting signals from the imaging system to a receiving system. Other devices and capsules may be used with the system and method of the present invention.

Capsule shaped device 10 includes body 100 which has an optical window 11 at one end, behind which are situated an imaging system 101, at least one illumination source 102 and a transmitter 103, for imaging the gastrointestinal tract and transmitting image signals to an external receiving system (not shown). According to other embodiments other in vivo sensors may be used and data from the sensors may be transmitted to an external receiving system. At the opposite end of the device body 100 is a cone shaped tail like moveable appendage 12. The moveable appendage 12 is made of pliant material, such as rubber or silicon, biocompatible plastic, or suitable metal, and may include a space such as space 13, typically, an internal space, for higher flexibility. A space may not be needed. The moveable appendage 12 is typically moveably coupled to the device body 100 through, for example, a lever system that includes bar 16, rod 15 and joint 17.

Bar 16 may be moved by an actuator 18, which may be any actuator suitable for use in the invention. For example, the actuator 18 may be a piezoelectric actuator such as the piezoelectric "Nanomotion" crystals by P.M.G, Medica, that are capable of moving bar 16, which, in turn moves rod 15. Alternatively, the actuator 18 may be an electromagnet that creates an electromagnetic field along both sides of rod 15 or it may be a memory alloy that changes its shape under application of voltage or temperature. Other actuators may be used. Alternatively, an actuator may not be needed. Rod 15 is typically anchored to the device body 100 at joint 17 and is capable of movement, for example, but not limited to, lateral movement as indicated by arrows a and b. Joint 17 provides a pivotal point for rod 15 and is flexible enough to allow the movement initiated at bar 16 to be conveyed to the moveable appendage 12. In one embodiment of the invention, joint 17 is an elastic foil through which rod 15, which is a metal wire, is inserted. Optionally, joint 17 may provide a seal so that fluids cannot enter the inside of the device 10.

Figure 2:
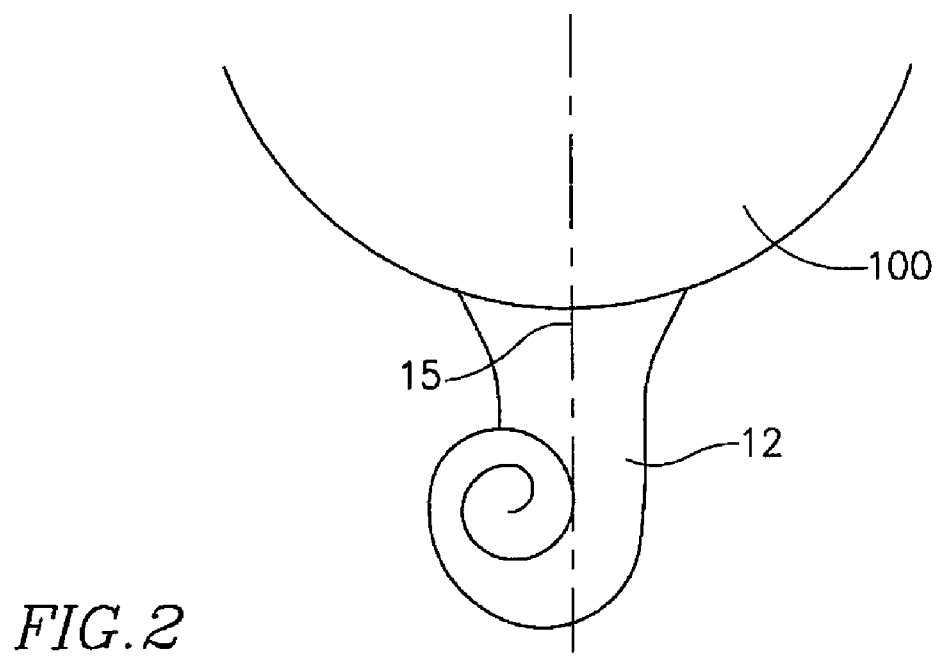
FIG. 2 is a schematic illustration of an object that is movable in a body lumen, in accordance with another embodiment of the invention.

In another embodiment of the invention schematically described in FIG. 2, the moveable appendage 12 that is attached to a device body 100, is compactly packaged or initially in a relatively compact state compared to an extended state, such as, by being rolled up. The compact packaging may include the rod 15, in which case, rod 15 is made of a suitable flexible material such as rubber or silicon, biocompatible metal or plastic, that, for example snaps into a rigid configuration once it is let out of its packaging.

The compact packaging of the moveable appendage 12 may be effected by encapsulation, such as encapsulation within a gelatin capsule, that dissolves according to specific parameters, such as time, pH, temperature, electromagnetic field, etc. Thus, the device is compactly configured in some parts of the body lumen but has an extended appendage in other parts of the lumen. It will be appreciated that the configuration of the device according to embodiments of the invention can be controlled externally and/or in accordance with the conditions in the body lumen environment.

Figure 3:
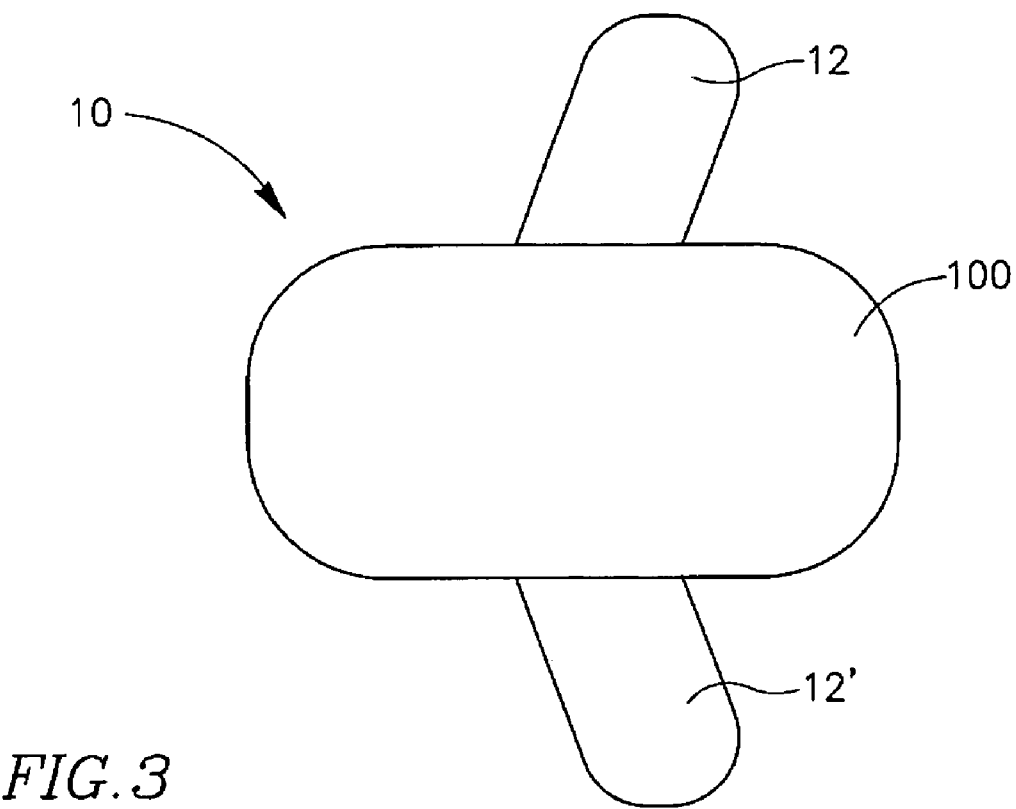
FIG. 3 is a schematic illustration of an object that is movable in a body lumen, in accordance with yet another embodiment of the invention.

In another embodiment of the invention schematically described in FIG. 3, the device 10 possesses more than one moveable appendage (12 and 12') attached to the device body 100. Appendages 12 and 12' may be moved simultaneously or alternatively so as to most effectively move the device 10 in the body lumen.

The embodiment schematically illustrated in FIG. 3 may include a lever system such as that described in FIG. 1. Alternatively, the moveable appendage 12 and/or 12' may be made of a suitable bimorph material, such as poly vinyl. The moveable appendages 12 and/or 12' could change their configuration in accordance with different conditions, as known in the art, such as a temperature or electric voltage gradient. Each configuration change of the moveable appendages 12 and/or 12' would move the appendages and thus move device 10, for example, as described above. It will be appreciated that the conditions required to cause a configuration change, such as creating a temperature or electric voltage gradient in the vicinity of the movable appendages (including in the appendages themselves), can be externally controlled. An external or internal unit may determine that the device has not moved for a predetermined period of time. Accordingly, a command can be sent (either from an internal logic or using wireless transmission from an external source) for activating the configuration change. Activation of the configuration change will cause movement of the device in the body lumen.

The moveable appendages are typically sized and designed such that they are large enough to impart movement to the device, on one hand, but do not hinder the device movement in the body lumen, on the other. For example, the moveable appendage may be the size of a few mm up to about 25 mm on a device of about 30 mm. Preferably the appendage is about ⅘ of the size of the device. Other dimensions are possible.

In one embodiment of the invention, device 10 is swallowed by a patient and an imaging system within the device is activated. The device 10, which is moved passively through the patient's digestive tract due to natural peristalsis of the small intestine, collects images of the patient's digestive tract and transmits them to an external recorder. When the device 10 reaches larger lumens within the digestive tract, such as the stomach or the large intestine, it is possible that the natural contractions of the digestive tract walls will no longer be effective in moving the device 10. The device's 10 movement may be delayed, for example in the cecum, a sac like evagination at the beginning of the large intestine. Movement of the moveable appendage can then be initiated to dislodge the device from the secum and to enable continued movement of the device through the large intestine. Movement of the moveable appendage in the intestine environment might facilitate movement of the device through the intestine, such as by propulsion. However, if the moveable appendage contacts the intestine wall while it is moved it will more effectively dislodge the device from its place and assist in pushing it along the intestine. Thus, an imaging device in accordance with an embodiment of the invention can effectively obtain images of the entire gastrointestinal tract.

Figure 4:
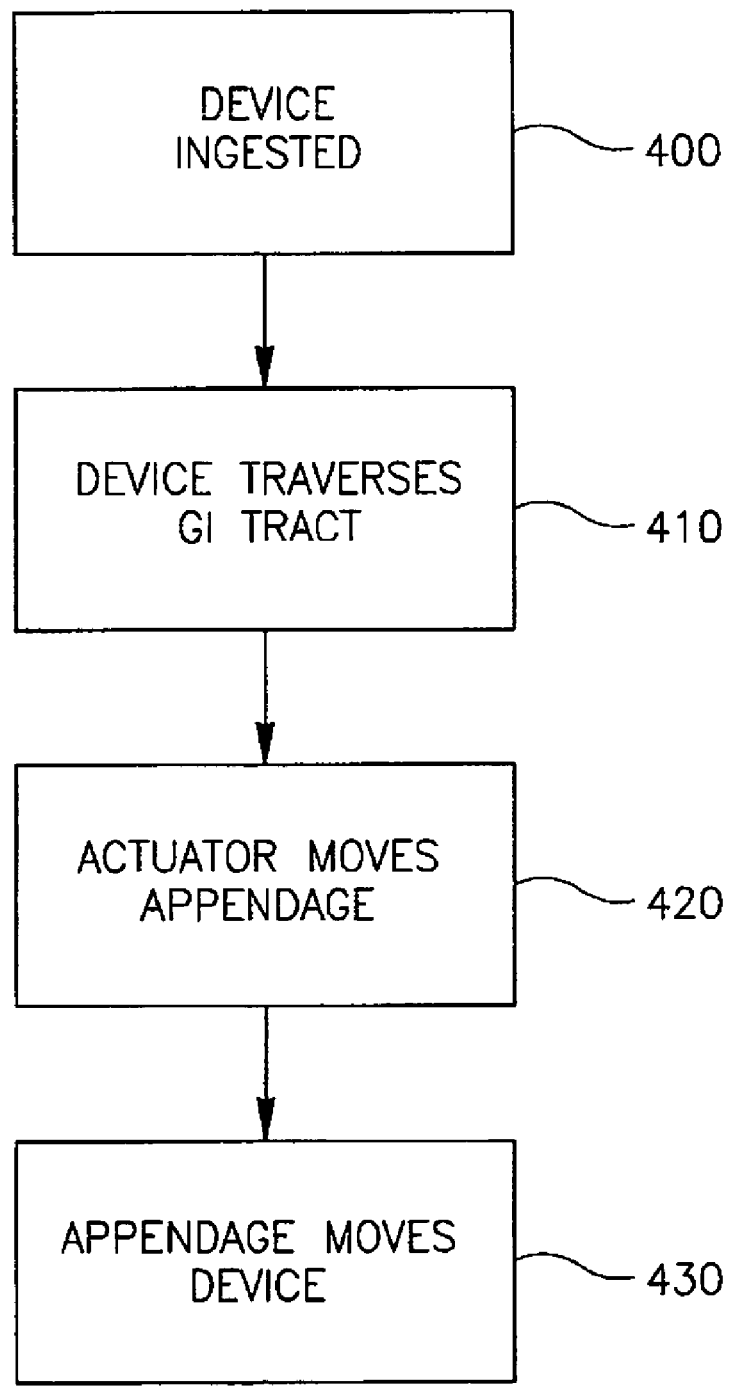
FIG. 4 is a schematic presentation of steps of a method according to an embodiment of the present invention.

FIG. 4 depicts a series of steps of a method according to an embodiment of the present invention.

In step 400, a device is ingested by a subject, such as a human patient.

In step 410, the device traverses the gastrointestinal tract.

In step 420, an actuator in the device moves a moveable appendage. The actuator may operate in response to, for example, a signal from the device, or, may, for example, "automatically", as part of a material's memory for a certain shape.

In step 430, the appendage moves the device.

In other embodiments, other series of steps may be used.

Following are non-limiting examples of some embodiments of the invention.

EXAMPLES

Tests were carried out in order to confirm the capability of a moveable appendage to dislodge a capsule shaped device and move it around within the bowel. However, a person skilled in the art can adjust or adapt the procedures exemplified below in accordance with specific object and/or body lumen requirements.

Example 1

An empty capsule with a movable tail like appendage covered by a soft cover of rubber or silicone is loaded with a 4 gr ballast. Two or three internal batteries or an external power source connected by fine flexible wires are used to enable a continuous full span motion of 1 Hz (possibly at an adjustable rate). Operation of this capsule assists in the fine tuning the mechanical/dynamic design of the device and in optimization of the appendage length and other dimensions.

Example 2

An empty capsule with a movable tail like appendage covered by a soft cover of rubber or silicone is loaded with a 4 gr ballast. An adhesive for sealing the cover to the capsule body is used. 2-3 internal batteries are used to operate the capsule at a controlled motion of 0.1-2 Hz at an adjustable/selectable rate and amplitude. The capsule is placed in a segment of a live bowel to observe the interaction between the tissue and movable appendage. The capsule is further placed within a flow model of the colon (made of rubber) to monitor its functionality when immersed in liquid and effected by gravity and position of the colon. By this procedure repositioning of the capsule by the appendage movement is observed and optimization of the rate and span of the moveable appendage is enabled.

Example 3

An empty capsule with a movable tail like appendage covered by a soft cover of rubber or silicone is loaded with a 4 gr ballast. An adhesive for sealing the cover to the capsule body is used. 2-3 internal batteries operating for at least 4 hours are used to operate the capsule at a controlled motion of 0.1-2 Hz at an adjustable/selectable rate and amplitude (before insertion). The capsule is inserted into the bowel of a sedated animal. Its location is monitored and recorded by X-ray. Opaque solution is injected into the bowel to delineate the bowel volume. By this procedure repositioning of the capsule within the bowel by the appendage movement and advancement of the capsule along the bowel are observed.

It will be appreciated by persons skilled in the art that the present invention is not limited to what has been particularly shown and described hereinabove. Rather the scope of the present invention is defined only by the claims which follow.

The invention claimed is:

1. An in vivo imaging system comprising:
an autonomous device comprising:
   a body comprising an image sensor, wherein said body has a longitudinal axis with a leading end and a trailing end;
   a movable appendage having a shape different from that of the body, wherein said appendage is moveably coupled with the body about an axis about a pivot joint at the trailing end of said body; and
   an actuator to move the appendage at an adjustable rate and amplitude about said axis so as to convey adjustable movement to the body,
a processor configured to determine movement of said autonomous device within a body lumen and to activate said actuator if said autonomous device has not moved within a predetermined period of time.

2. An in vivo imaging system according to claim 1 wherein the appendage includes pliant material.

3. An in vivo imaging system according to claim 1 wherein the object body and the appendage are coupled through a lever system.

4. An in vivo imaging system according to claim 1 wherein the device comprises an optical window.

5. An in vivo imaging system according to claim 1 wherein the device comprises an illumination source.

6. An in vivo imaging system according to claim 1 wherein the device comprises a transmitter for transmitting image signals to an external receiving system.

7. An in vivo imaging system according to claim 1 wherein the appendage is initially packaged in a compact state.

8. An in vivo imaging system according to claim 1 wherein the appendage is configured to change shape in response to an electrical stimulus.

9. An in vivo imaging system according to claim 1 wherein the appendage is configured to change shape in response to change in an in-vivo condition.

10. An in vivo imaging system according to claim 1 wherein the appendage is to press against an endo-luminal wall to dislodge the device from a position on the endo-luminal wall.

11. The in vivo imaging system according to claim 1 wherein the actuator is responsive to a wirelessly transmitted command.

12. An in vivo imaging system according to claim 1 wherein the movable appendage comprises two movable appendages, one at either side of said body.

13. An in vivo imaging system according to claim 2 wherein the movable appendage comprises said pliant material covering a rigid core.

14. An in vivo imaging system according to claim 1 wherein the axis of motion of said movable appendage intersects with a wall of said body.

15. An in vivo imaging system according to claim 14 wherein the movable appendage comprises a space on either side of said axis to provide flexibility of said appendage with respect to said body wall.

\* \* \* \* \*